United States Patent [19]

Tancrell

[11] 4,320,660

[45] *Mar. 23, 1982

[54] FRESNEL FOCUSSED IMAGING SYSTEM

[75] Inventor: Roger H. Tancrell, Cambridge, Mass.

[73] Assignee: Raytheon Company, Lexington, Mass.

[*] Notice: The portion of the term of this patent subsequent to Mar. 27, 1996, has been disclaimed.

[21] Appl. No.: 155,324

[22] Filed: Jun. 2, 1980

Related U.S. Application Data

[60] Division of Ser. No. 962,571, Nov. 20, 1978, Pat. No. 4,228,686, which is a continuation-in-part of Ser. No. 866,325, Jan. 3, 1978, Pat. No. 4,145,931.

[51] Int. Cl.³ .......................................... G01N 29/00
[52] U.S. Cl. ..................................................... 73/626
[58] Field of Search ................. 73/626, 602, 610, 612, 73/613, 618; 128/660; 310/316–319, 334, 336; 367/103, 105, 137, 138

[56] References Cited

U.S. PATENT DOCUMENTS

| | | | |
|---|---|---|---|
| 3,504,368 | 3/1970 | Ruben | 343/701 |
| 3,805,596 | 4/1974 | Klahr | 73/626 |
| 3,911,730 | 10/1975 | Niklas | 73/626 |
| 3,919,683 | 11/1975 | Itamura et al. | 73/626 |
| 3,956,735 | 5/1976 | Cassonnet | 364/200 |
| 4,080,838 | 3/1978 | Kuroda et al. | 73/612 |

OTHER PUBLICATIONS

P. Alais et al., "Fresnel Zone Focusing of Linear Arrays Applied to B and C Echography", Acoustical Holography, vol. 7, pp. 509–522, Aug. 1976.

*Primary Examiner*—Stephen A. Kreitman
*Attorney, Agent, or Firm*—Martin M. Santa; Joseph D. Pannone

[57] ABSTRACT

An imaging system, particularly useful for acoustic medical diagonsis of a human subject, utilizes an array of radiating elements or sonic transducers located side-by-side and positioned along the subject. Signals received by the transducer are applied to a pair of pattern generation circuits which weight the individual signals by factors of +1, −1 or 0. Graphs of the weighting factors as a function of transducer location have the likeness of cosinusoidal and sinusoidal Fresnel patterns, these patterns being produced by the two circuits. Upon reception of signals, the weighted signals of each pattern are summed together, multiplied by cosinusoidal and sinusoidal reference signals and then summed together to provide a radiation pattern which converges from the array to a focal point in front of the array while eliminating a diverging pattern from a virtual focus behind the array. For transmission, sinusoidal and cosinusoidal signals are weighted by the Fresnel factors, summed together and applied to the transducers.

7 Claims, 15 Drawing Figures

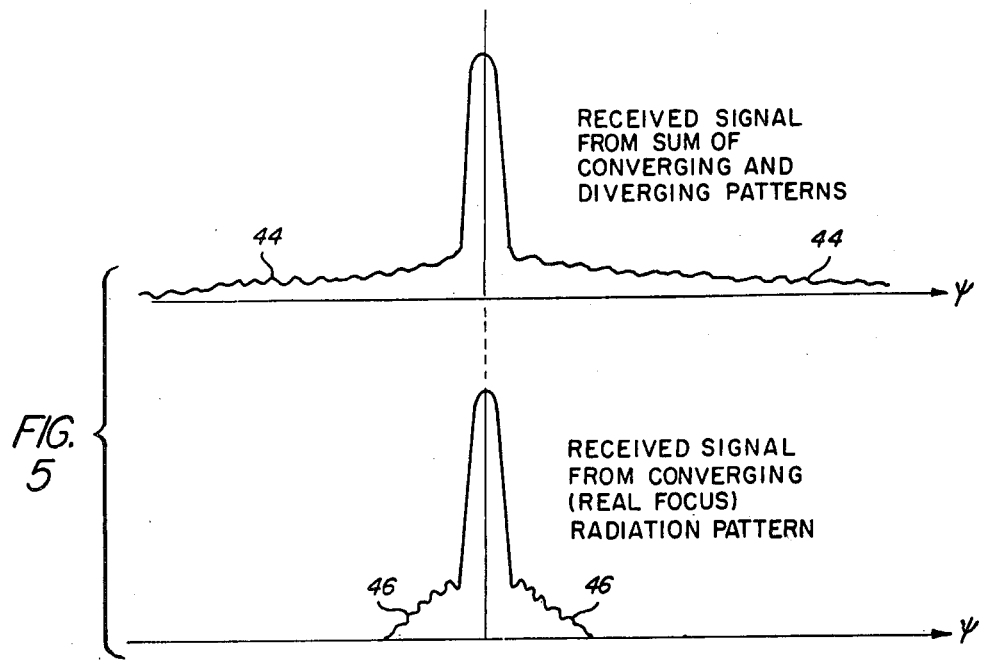
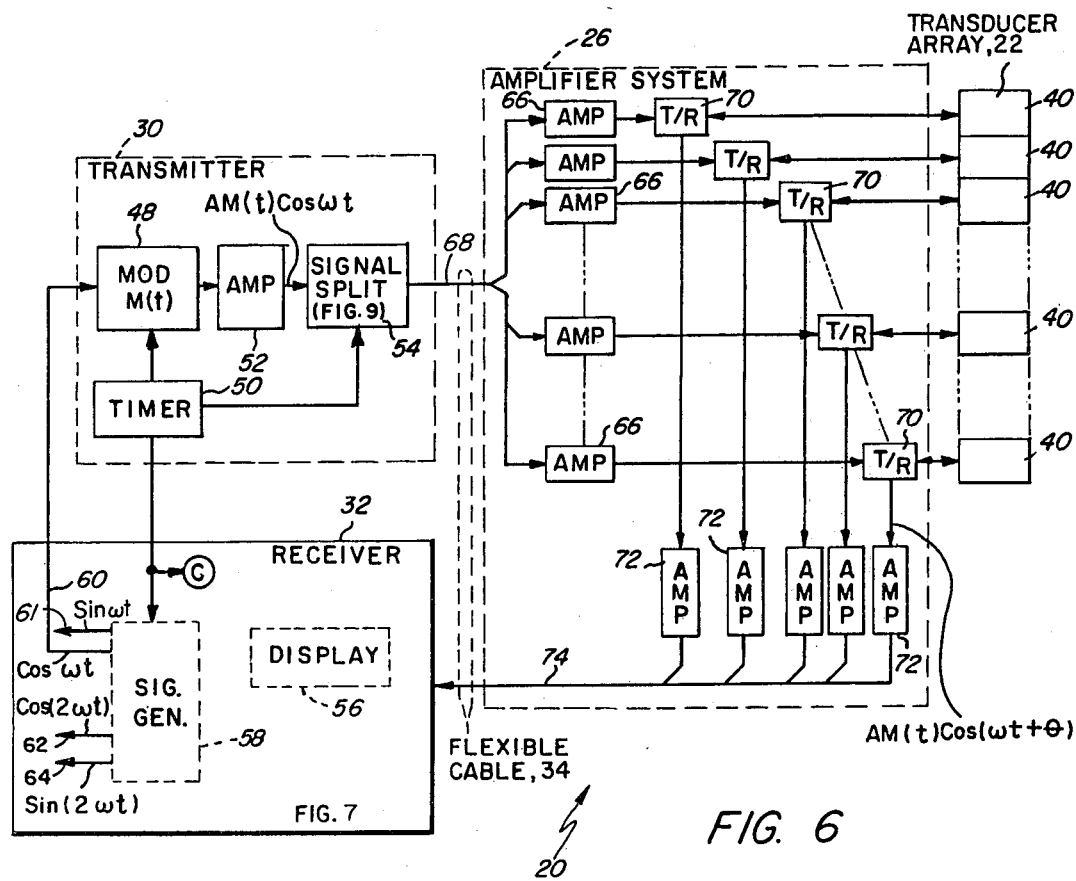

FRESNEL FOCUSSED IMAGING SYSTEM

CROSS-REFERENCE TO RELATED APPLICATIONS

This is a division of co-pending application Ser. No. 962,571, filed Nov. 20, 1978, now U.S. Pat. No. 4,228,686, which was a continuation in part of co-pending application Ser. No. 866,325, filed Jan. 3, 1978, now U.S. Pat. No. 4,145,931.

BACKGROUND OF THE INVENTION

This invention relates to an imaging system employing an array of radiation detectors and, more particularly, the use of a Fresnel pattern impressed upon signals received by the detectors to provide for imaging as in the case of the sonic imaging of a human subject.

Fresnel masking has been utilized in both electromagnetic and sonic imaging systems. With respect to electromagnetic imaging systems, a Fresnel pattern is disclosed in the U.S. Pat. No. 3,263,079 which issued to L. N. Mertz and N. O. Young on July 26, 1966 wherein the pattern is utilized for forming the image of stars in the sky. The use of a Fresnel pattern in nuclear medicine for forming an image of a radioactive source is disclosed in the U.S. Pat. No. 3,936,639 which issued in the name of H. H. Barrett on Feb. 3, 1976. The use of a Fresnel pattern impressed upon the signals of sonic radiation detectors is disclosed in the U.S. Pat. No. 3,911,730 which issued in the name of L. Niklas on Oct. 14, 1975 wherein the energization of groups of radiation detectors, or transducers, is employed following the arrangement of a Fresnel pattern in at least one dimension. The use of an ultrasonic imaging scanner for imaging organs of the human body is disclosed in the U.S. Pat. No. 3,805,596 which issued in the name of C. N. Klahr on Apr. 23, 1974.

The use of the Fresnel pattern for sonic imaging systems is advantageous in that the Fresnel pattern provides for the focussing of the sonic radiation in the manner of a lens. A problem arises in that with systems of the prior art, the Fresnel pattern, whether it be utilized with a one dimensional line array or in a two dimensional array, produces the effect of both a converging pattern of radiation which converges toward a focal point in the subject in front of the array as well as a diverging radiation pattern which emanates from a virtual focus located behind the array. The energy content of signals produced by the transducers in response to incident sonic energy from the diverging radiation pattern approximately equals that of the energy content of signals associated with the desired converging pattern. As a result, there is substantial unwanted noise which degrades an image of the subject obtained with the converging radiation pattern.

SUMMARY OF THE INVENTION

The aforementioned problem is overcome and other advantages are provided by an imaging system in conjunction with radiating elements such as sonic transducers wherein, in accordance with the invention, a pair of Fresnel patterns is impressed upon signals of the transducers, one Fresnel pattern being a cosinusoidal Fresnel pattern while the second is a sinusoidal Fresnel pattern, the combining signals of the two patterns to produce a resultant radiation pattern of the array wherein the aforementioned undesirable diverging pattern is absent. Thereby, upon imaging a subject, such as a human being, various sites within the subject are viewed by the converging radiation pattern to produce a sharp image of each site without the interference associated with noise from the diverging radiation pattern. The imaging system of the invention is equally applicable to an array of detectors of electromagnetic radiation as well as to an array of detectors of sonic radiation. However, for convenience in describing the invention, reference will be made to sonic transducers, it being understood that the description is equally applicable to the case of electromagnetic radiation.

Each of the aforementioned Fresnel patterns is impressed upon signals produced by the transducers in response to sound waves incident thereupon, or applied to the transducers during transmission, by a set of multipliers which are coupled to individual ones of the transducers. Each multiplier multiplies the polarity of a transducer signal by a factor of +1, −1 or 0. In a preferred embodiment of the invention, each of the multipliers comprises an inverting amplifier with a selector switch which selects either the positive or negative output signals of the amplifier or provides for the grounding of the signal to provide the value of 0. The multiplication factor for each transducer signal is selected in accordance with the location of the respective transducers within the array so that a graph of the multiplication factors, as a function of transducer location, has the appearance of a square wave approximation to a Fresnel pattern. A pair of the multipliers is coupled to each of the transducers so that the aforementioned pair of Fresnel patterns may be generated simultaneously.

For receiving signals from the subject, the sum of the products of the multipliers for the cosinusoidal Fresnel patterns are summed together and multiplied by a cosinusoidal reference signal. Similarly, the products of the multipliers for the sinusoidal Fresnel pattern are summed together and multiplied by a sinusoidal reference signal. The amplitudes of the products resulting from the multiplications with the two reference signals are then equalized and summed together. The resultant sum is then passed through a band pass filter to remove harmonics of the multiplication operation and then passed to a display whereby the various sites within the subject may be seen. A controller of the multiplying factors comprises a memory which is sequentially addressed in accordance with the range or depth within the subject of the respective sites for altering the Fresnel pattern for focussing at the respective sites whereby each of the sites is brought into sharp focus. At the conclusion of the displaying of sites along a normal to a group of transducers utilized in the Fresnel pattern, the multiplying factors are selected so as to shift the Fresnel pattern sideways along the array so as to focus on a contiguous portion of the subject. Continuous side-stepping of the Fresnel pattern permits the viewing of a swath or rectangular slice of the subject.

To transmit signals from the transducers, sinusoidal and cosinusoidal components of the signals are each weighted in accordance with Fresnel patterns and combined to produce the signals for transmission by each of the transducers.

BRIEF DESCRIPTION OF THE DRAWINGS

The aforementioned aspects and other features of the invention are explained in the following description taken in connection with the accompanying drawings wherein:

FIG. 5 shows two graphs of the intensity of echo strength from a site within the subject as a function of angle about a normal to the face of the transducer array, the normals and the angles being seen in the fourth graph of FIG. 4, the second graph showing the reduction in noise resulting from the cancellation of signals of the diverging beam in accordance with the invention;

FIG. 6 shows a block diagram disclosing the electrical connections between the transducer array and a transmitter and a receiver of FIG. 1;

DESCRIPTION OF THE PREFERRED EMBODIMENT

Figure 1:
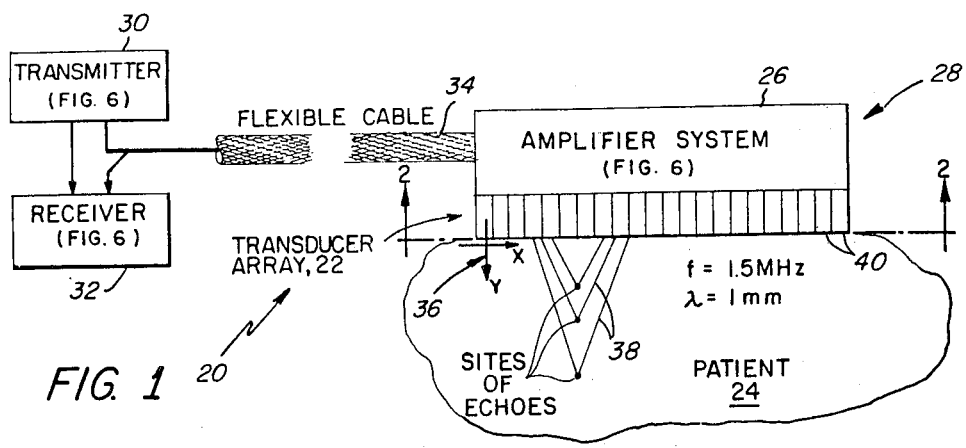
FIG. 1 shows a transducer array of the invention positioned in contact with a subject, such as a portion of a patient in a hospital, the transducer array being coupled to a transmitter and receiver for the transmission of acoustic signals into the subject and the reception of echoes therefrom.

Referring now to FIG. 1, there is seen an imaging system 20 which, in accordance with the invention, comprises a transducer array 22 positioned in contact with a subject 24, and an amplifier system 26. The amplifier system 26 and the transducer array 22 are incorporated within a common module 28. The system 20 further comprises a transmitter 30, a receiver 32 and a flexible cable 34 joining the transmitter 30 and the receiver 32 with the module 28. A coordinate system 36 having X and Y axes is situated at a corner of the module 28 at the surface of the subject 24 for locating sites within the subject 24, the X axis measuring horizontal positions along the interface between the module 28 and the subject 24 while the Y axis measures depth into the subject 24 from the face of the transducer array 22. Also shown are sound rays 38 emanating from sites within the subject 24 to illustrate propagation of echoes from the sites to the transducers of the active portion of the array 22.

As will be seen subsequently, the transmitter 30 transmits a pulse electrical signal via the cable 34 and the amplifier system 26 to the transducer array 22, individual transducers 40 of the array 22 being selectively energized by the pulse signal for transmitting a sonic pulse signal toward the sites in the subject 24. Echo signals propagating from the sites back to the array 22 are coupled via the amplifier system 26 to the receiver 32 which performs a Fresnel multiplication operation and displays the resultant echo. The flexible cable 34 permits the positioning of the module 28 at any desired location on the subject 24.

Figure 2:
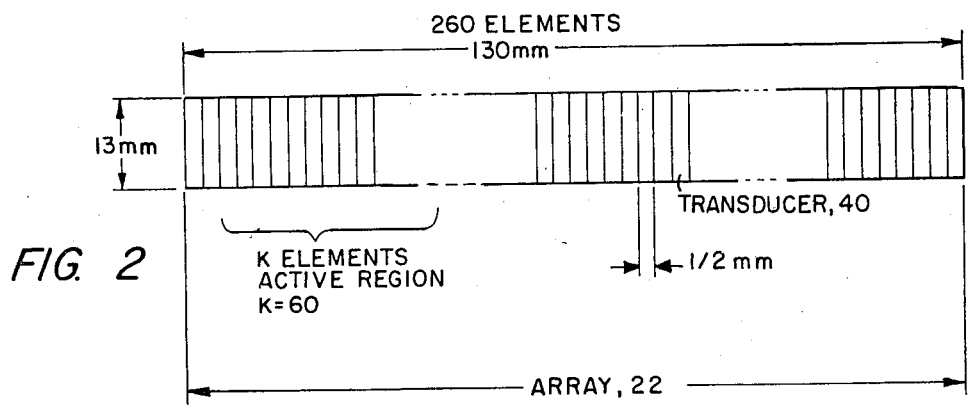
FIG. 2 shows a plan view of the transducer array of FIG. 1 taken along the lines 2—2 of FIG. 1.

Referring also to FIG. 2, the dimensions of an exemplary array 22 are presented. The array is seen to have a width of 13 mm (millimeters), a length of 130 mm, and includes 260 elements, each element being one of the transducers 40 of FIG. 1. As noted in FIG. 1, the frequency of transmission of the sonic energy is given as 1.5 MHz (megahertz) with a wavelength of 1 mm within the subject 24. Each transducer 40 has a front face in the shape of a narrow rectangle wherein the length of each face is 13 mm and the width thereof is $\frac{1}{2}$ mm. Also, by way of example in receiving sonic energy, a group of 60 elements is shown as the active region whereby the Fresnel patterns are formed.

Figure 3:
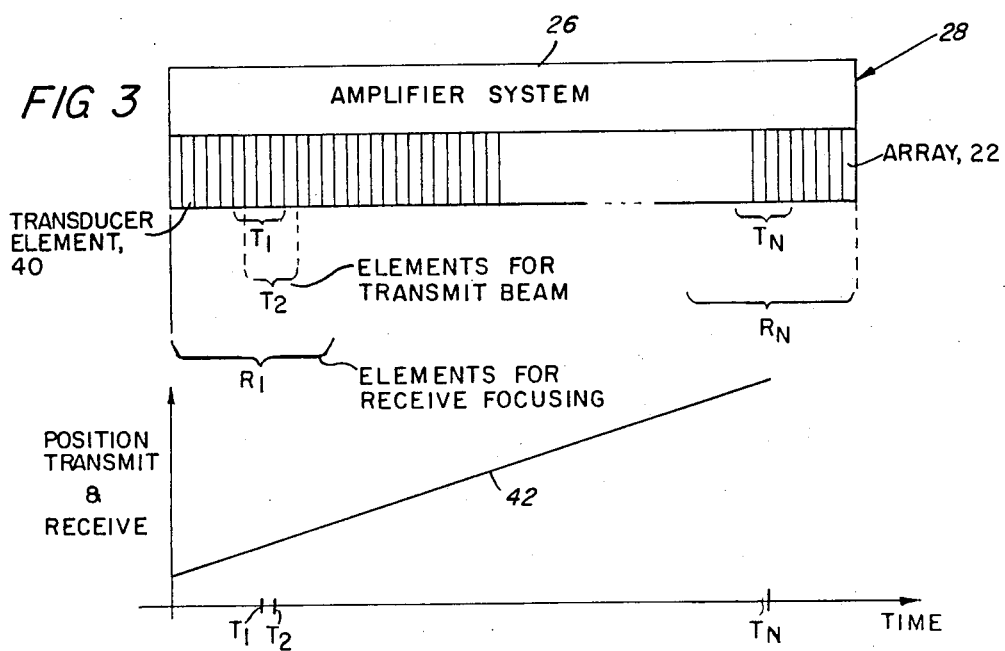
FIG. 3 shows a side view of the transducer array of FIG. 1 in combination with a graph displaying the temporal location of a group of transducers of the array actively participating in the formation of images of sites within the subject of FIG. 1, the graph portraying the side-stepping of the active region for scanning a rectangular swath of the subject.

Referring now to FIG. 3, the group of elements of the array 22 utilized for receiving sonic energy is enclosed by a bracket identified by the legend R while another group of elements utilized for transmitting sonic energy is enclosed by a bracket identified by the legend T. The subscripts 1 and 2 appended after the legends R and T indicate subsequent positions of the group of active elements with the subscript N indicating the final position of the receiving group at the end of a scan along the subject 24 of FIG. 1. The line 42 represents the linear stepping of the group of active elements after each scanning of a group of sites within the subject 24 on a line parallel to the Y axis. While the line 42 is shown as a straight line, it is to be understood that the actual positions of the centers of the groups of active elements are displaced a step at a time wherein each step may have the width of one transducer 40 or two or more of the transducers 40.

Figure 11:
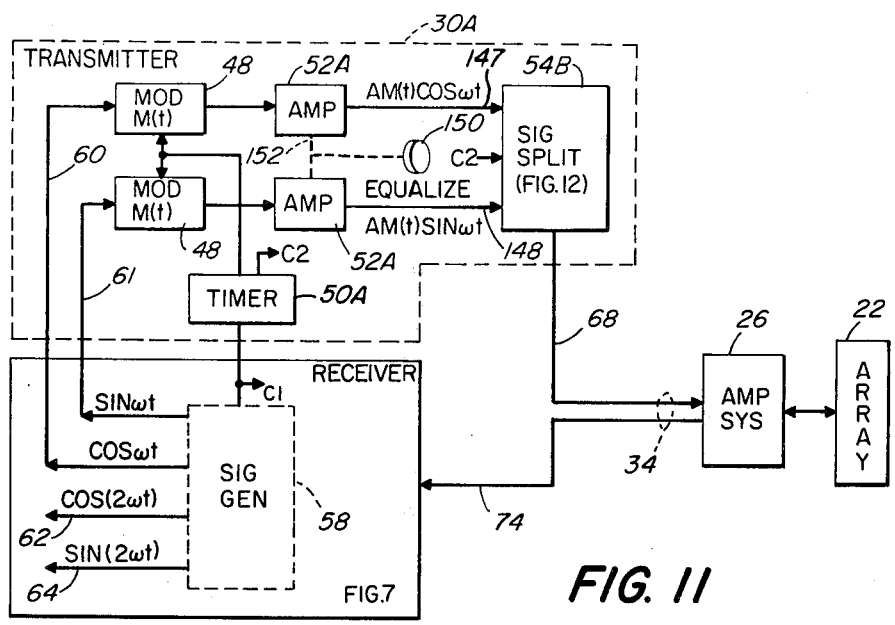
FIG. 11 shows a block diagram of an alternative embodiment of a transmitter of FIG. 6 for providing sinusoidal and cosinusoidal components of the signal.

The size of the group of elements T utilized for transmission is smaller than the receiving group R in the simple case wherein the transmitted beam is provided by energizing each transducer element of the group T with signals having a common amplitude and phase; the small group providing a narrower beam than a larger group in the region immediately in front of the array 22, the region being referred to as the near field or Fresnel region. In the more complex case to be described hereinafter with reference to FIG. 11, the size of the transmitting group T is generally equal to the size of the receiving group R since the system of FIG. 11 provides for energizing the transducer elements with signals modulated in accordance with a Fresnel pattern to focus the sonic radiation at a site within the subject 24.

Figure 4:
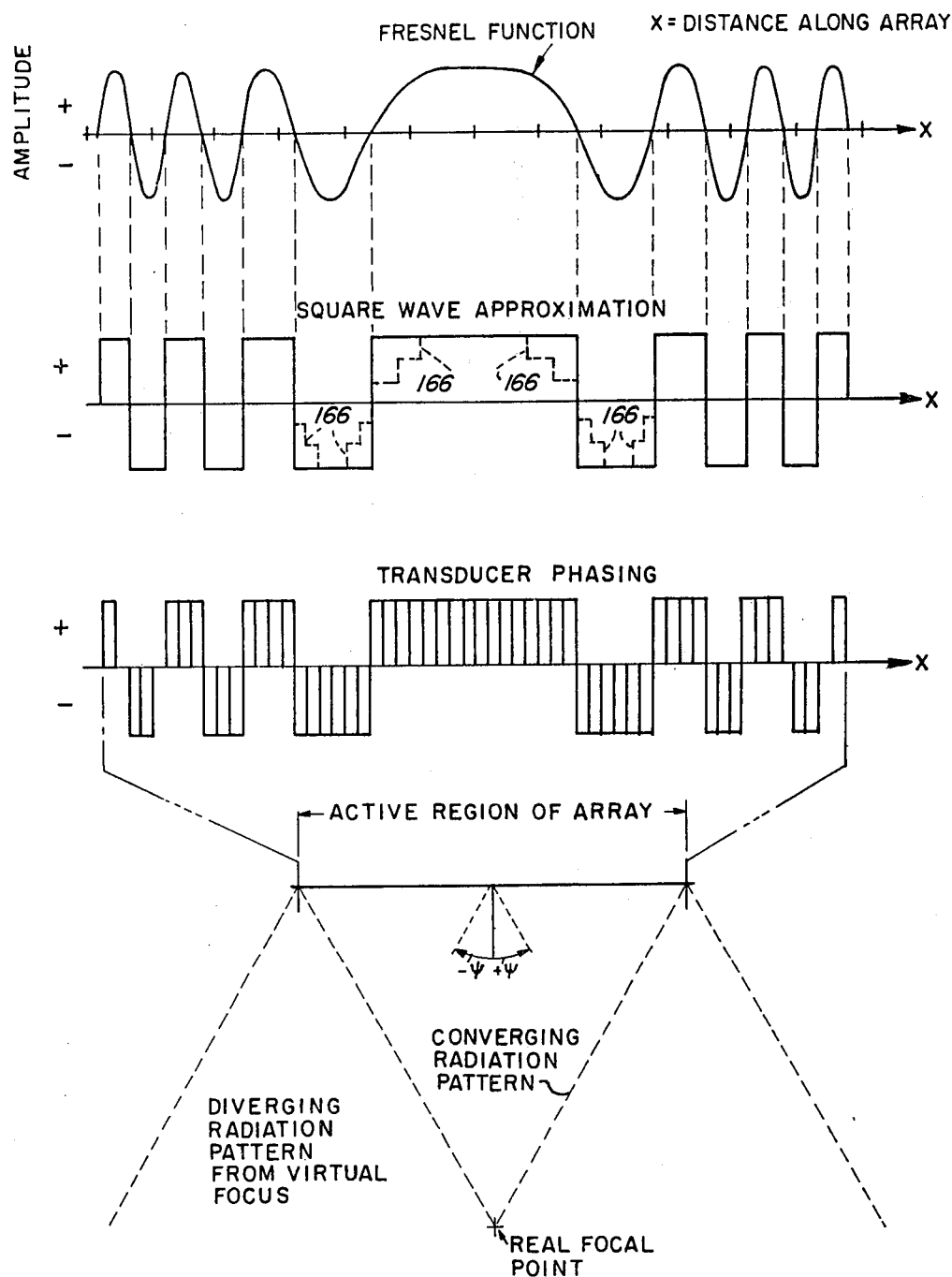
FIG. 4 shows a set of four graphs in registration with each other, the first graph showing a Fresnel function with the horizontal distance along the transducer array of FIG. 1 serving as a parameter thereof, the second graph showing a square wave approximation to the Fresnel function, the third graph showing the multiplication of the signals of individual ones of the transducers of the active region of the array wherein the polarity of the signals subsequent to the multiplication follows the pattern of the square wave approximation of the second graph, and the fourth graph shows the resultant converging radiation pattern, as well as the diverging radiation pattern which is obtained when only one Fresnel function is employed in the signal processing.

Referring now to FIG. 4, the first graph depicts a cosinusoidal Fresnel pattern constructed for a set of elements of the array 22 which comprises the active group of receiving elements. Thus, with reference to FIG. 2, wherein sixty transducers 40 serve as the active elements, the Fresnel pattern of the first graph of FIG. 4 encompasses the sixty elements. Similar comments apply to the second and third graphs which represent a square wave approximation to the Fresnel pattern. Furthermore, with reference to the third graph of FIG. 4, it is noted that the graph shows, by way of example, transducer signal samples that have been multiplied by zero as well as by $+1$ and $-1$. Thus, the positive values indicate a multiplication by $+1$, while the negative values indicate multiplication by the factor $-1$. It is also noted that the third graph shows a relatively large number of transducer elements of which the signals have a common phase within the central portion of the Fresnel function. Nearer the edges of the Fresnel function, the numbers of transducers involved in any one small band of the Fresnel function is relatively small with only one transducer element being shown for the last band. The multiplying factors utilized in the third graph produce the radiation pattern of the active region portrayed in the fourth graph wherein it is seen that there are two superposed radiation patterns. One of these superposed radiation patterns converges to a real focal point in front of the array 22 of FIG. 1 while the second of the superposed radiation pattern diverges from a virtual focus which would be located behind the array 22 of FIG. 1. In view of the fact that the cosinusoidal Fresnel pattern is an even function of distance along the face of the array 22 while the sinusoidal Fresnel pattern is an odd function of distance along the face of the array 22, the combination of the two patterns result in the removal of the diverging pattern so that, as a result of the signal processing of the invention, only the converging radiation pattern is utilized in forming images of the sites within the subject 24 of FIG. 1.

The two graphs of FIG. 5 show the radiation pattern after combination of the signals of the transducers of the array 22, the first graph relating to single one of the aforementioned Fresnel patterns while the second graph relates to the use of both cosinusoidal and sinusoidal Fresnel patterns. The horizontal axis of each graph represents the angle measured relative to a normal to the face of the array, the angles being identified relative to a normal in the fourth graph of FIG. 4. The first graph of FIG. 5 represents the prior art showing substantial noise in the skirts 44 of the radiation pattern. The skirts 46 of the second graph of FIG. 5 show greatly diminished energy content thereby indicating that the signal processing of the invention involving the use of the aforementioned pair of Fresnel patterns has greatly reduced the noise surrounding the desired signals from which the image of the subject 24 is composed. It is also noted that, with the aforementioned use of a Fresnel pattern in nuclear medicine, the imaging in the nuclear medicine case is based on a non-defraction of gamma rays while, in the present case of sonic imaging, defraction and interference phenomena of sonic waves produce the focussing of the radiation pattern upon a focal point in a manner analogous to the Fresnel focussing in optics.

Referring now to FIG. 6, the transmitter 30, the receiver 32 and the amplifier system 26 of FIG. 1 are presented in greater detail. The transmitter 30 is seen to comprise a modulator 48, a timer 50, an amplifier 52 and a signal splitter 54. The receiver 32 comprises a display 56 for portraying an image of the subject 24 of FIG. 1. The receiver 32 further comprises a signal generator 58 which provides on line 60 a cosinusoidal carrier of the signal transmitted by the array 22 as well as a sinusoidal carrier on line 61 for use in an alternative embodiment disclosed hereinafter with reference to FIG. 11 for focussing the sonic energy at a site within the subject 24. The generator 58 also provides a pair of reference signals on lines 62 and 64 which will be utilized in a manner to be described with reference to FIG. 8 for processing signals received by the array 22 to provide the image of the subject 24. The amplifier system 26 comprises a set of amplifiers 66 having their respective input terminals connected by lines seen fanning into the line 68 which is coupled to the signal splitter 54, a set of transmit-receive circuits 70 coupled between respective output terminals of the amplifiers 66 and the transducers 40 of the array 22, and a set of preamplifiers 72 coupled to respective ones of the circuits 70 for amplifying signals received by respective ones of the transducers 40, the output terminals of the preamplifiers 72 being coupled via lines which fan into line 74 for coupling via the cable 34 to the receiver 32.

The operation of the transmitter 30 and the operation of the receiver 32 are synchronized by clock signals provided by the timer 50. In response to the clock signals from the timer 50, the generator 58 applies the cosinusoidal carrier signal of line 60 to the modulator 48, and the modulator 48 applies an amplitude modulation in the form of a short pulse to the carrier signal. By way of example, the pulse duration provided by the modulator 48 is approximately 3 microseconds to provide four or five cycles of the carrier signal. The amplifier 52 amplifies the power of the pulsed signal of the modulator 48 for driving the signal splitter 54 which will be described with reference to FIG. 9. The two reference signals of the signal generator 58 on lines 62 and 64 are at double the frequency of the carrier signals, one of the reference signals having a cosinusoidal waveform and the other reference signal having a sinusoidal waveform. The signal splitter 54 selects a group of transducers 40, corresponding to the transmitting group of FIG. 3, and distributes the pulsed carrier signal from the amplifier 52 via a set of conductors represented by line 68 in the cable 34 to the respective ones of the amplifiers 66. The signal splitter 54, in using only the carrier of line 60, energizes equally each transducer 40 for focussing the sonic energy at infinity. The amplifiers 66 provide sufficient power to the pulsed carrier signals for driving the transducers 40 for insonifying the subject 24 of FIG. 1. The circuits 70 couple the transmitted signal from the respective amplifiers 66 to the transducers 40 while isolating the signals from the preamplifiers 72. The signals received by the transducers 40 are coupled via the circuits 70 and the preamplifiers 72 to the receiver 32.

Figure 7:
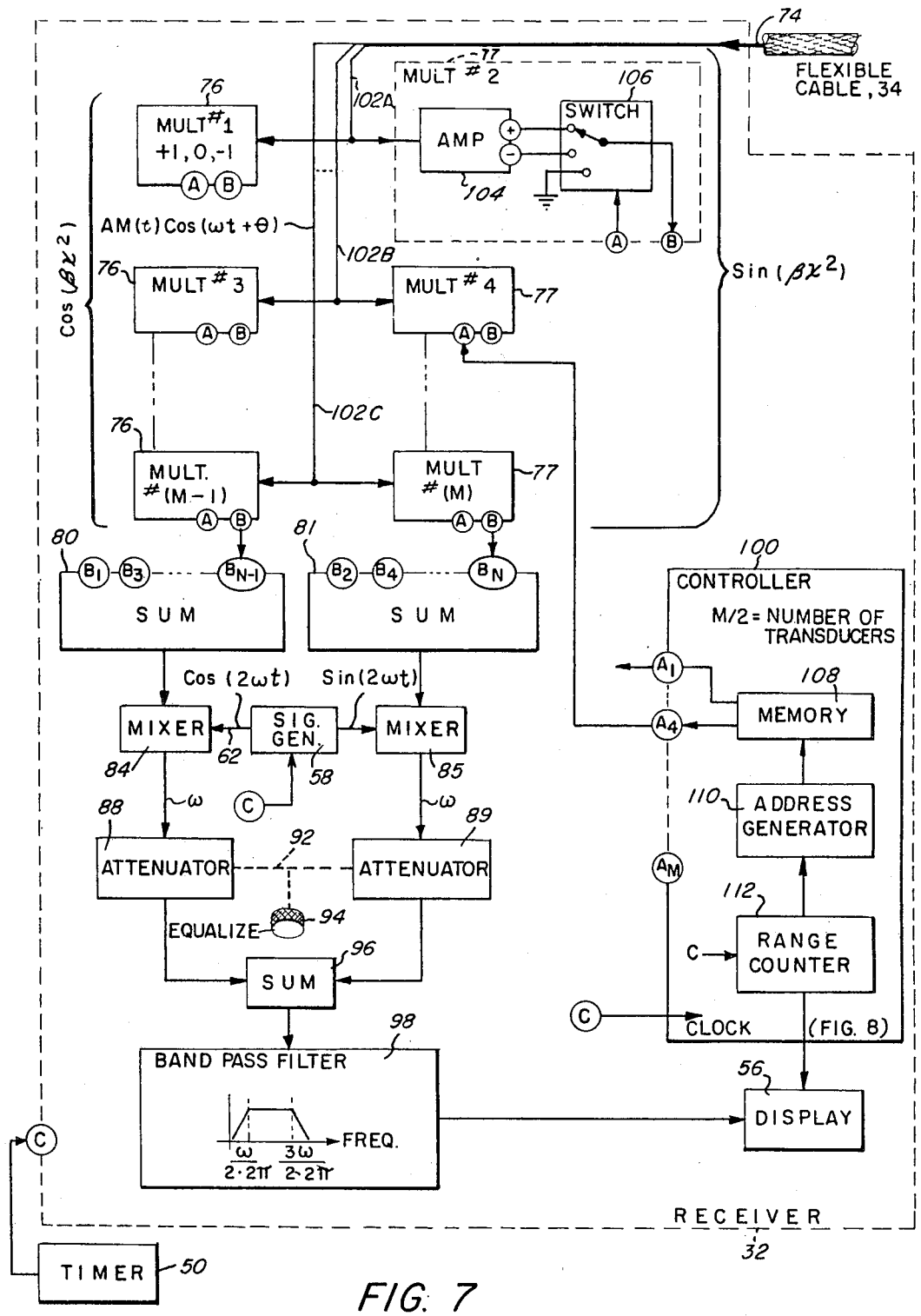
FIG. 7 is a block diagram of the receiver of FIGS. 1 and 6 disclosing the multiplication of the transducer signals to provide the pair of Fresnel patterns.

Referring now to FIG. 7, there is seen a detailed block diagram of the receiver 32 of FIGS. 1 and 6. Line 74 of the cable 34 is seen to be coupled to the receiver 32 as well as clock signals at terminal C from the timer 50 as was noted hereinabove with reference to FIG. 6. The receiver 32 comprises a first set of multipliers 76, a second set of multipliers 77, summers 80 and 81, mixers 84 and 85, attenuators 88 and 89 which are mechanically coupled via line 92 to a knob 94, a summer 96, a bandpass filter 98, a controller 100, and the display 56 and the signal generator 58 which were previously seen in FIG. 6. Individual lines 102A–C, which fan out from the cable represented by the line 74, each carry the signal of one of the transducers 40 of FIG. 6, and each is coupled to a pair of multipliers 76 and 77. For example, the line 102A is coupled to multiplier #1 and multiplier #2. The line 102B is coupled to the multiplier #3 and the multiplier #4. There are a total of M multipliers 76–77 where M is equal to twice the number of transducers 40.

The set of multipliers 76, this comprising the odd numbered multipliers, provides multiplication by the set of factors corresponding to the cosinusoidal Fresnel pattern and may be referred to hereinafter as the cosine branch. The set of multipliers 77, this being the even numbered multipliers, provides multiplication by the set of factors corresponding to the sinusoidal Fresnel pattern and may be referred to hereinafter as the sine branch. Thus, the signal from each transducer is applied to one multiplier of each set. Thereby, each transducer 40 of the active region for receiving radiation, as disclosed in FIG. 3, provides a contribution to the generation of the cosinusoidal Fresnel pattern and the sinusoidal Fresnel pattern. The product of each of the multipliers 76–77 appears at terminal B, the input terminals of the summers 80–81 being similarly labeled with the legend B but being further identified by the numerals corresponding to the individual ones of the multipliers 76–77. Thus, terminal B of multiplier #1 is connected to terminal B1 of the summer 80, with similar connections being applied to the other multipliers such as the connection of terminal B of the multiplier #4 to terminal B4 of the summer 81. In this way, the products of each of the odd numbered multipliers 76 are summed together by the summer 80, and the products of each of the even numbered multipliers 77 are summed together by the summer 81.

Figure 8:
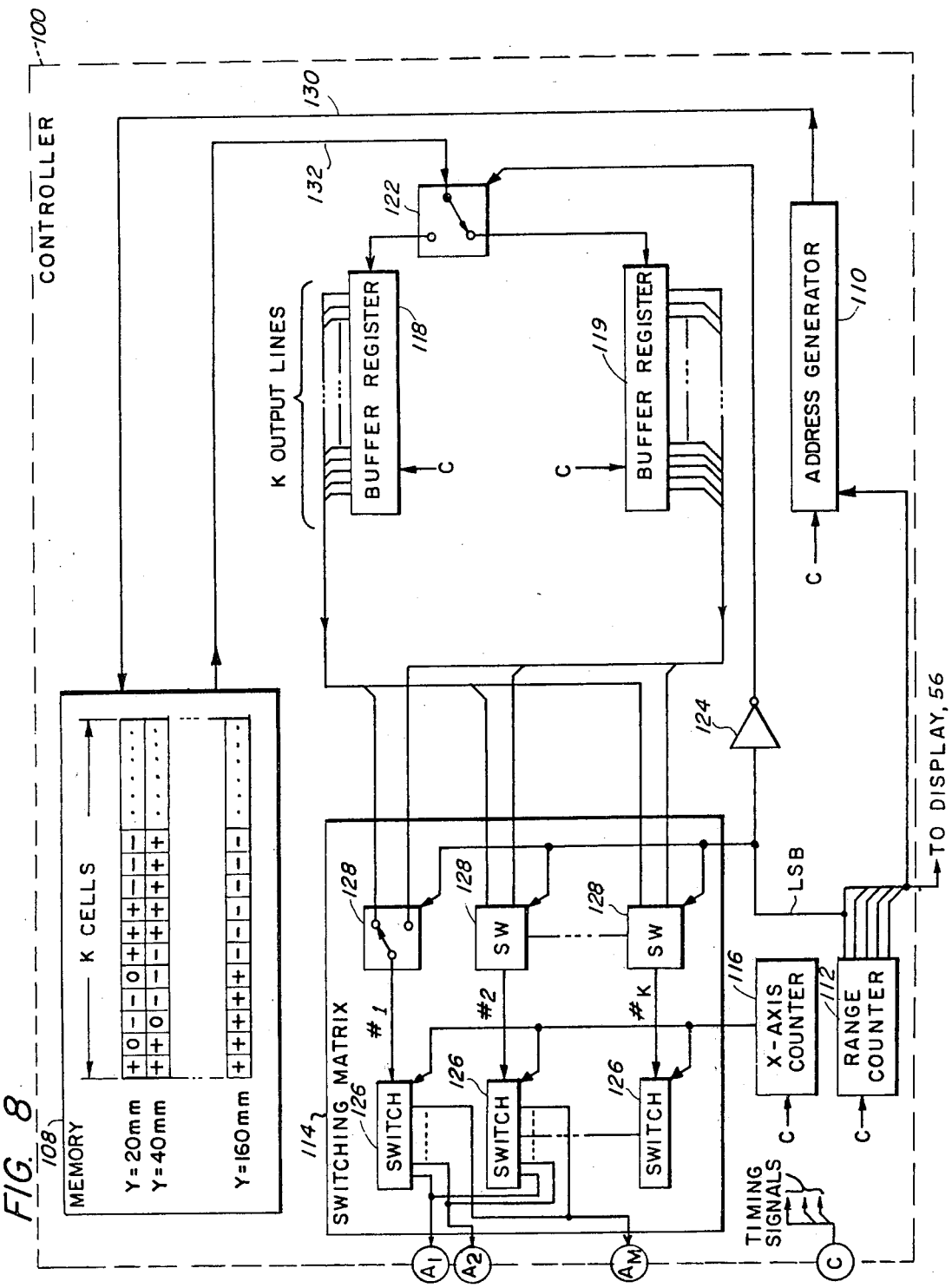
FIG. 8 is a block diagram of a controller of the multiplying factors of FIG. 7, the controller including a memory storing the multiplication factors for the group of active transducers and a switching matrix for redirecting the factors as the group of active transducers is displaced sideways along the array for scanning the subject.

Each of the multipliers 76–77 provides multiplication by a factor of +1, −1 or 0 as is shown in the block representing the multiplier #1. Each of the multipliers is comprised of an amplifier 104 and a switch 106 as is shown in the block representing the multiplier #2. The amplifier 104 provides positive and negative polarities of the signal at its input terminal, such as a signal on line 102A, the signals of positive and negative polarity being coupled to two input terminals of the switch 106. A third input terminal of the switch 106 is grounded. Terminal B of the multipliers 76–77 is selectively coupled by the switch 106 to one of the output terminals of the amplifier 104 whereby the product appearing at terminal B includes one of the aforementioned multiplying factors. The switch 106 in each of the multipliers 76–77 is controlled via a signal, such as a two-bit digital signal, at terminal A. The signals coupled to the terminals A in each of the multipliers 76–77 are provided by the controller 100 which is seen to have a set of output terminals identified by the legend A, the identification of the output terminals further including the numerals 1–M to identify the specific one of the multipliers 76–77 to which the switch control signal is being applied. The controller 100 is described briefly in FIG. 7 and in greater detail in FIG. 8, FIG. 7 showing a memory 108, an address generator 110 and a range counter 112. In accordance with the range of depth of a site within the subject 24 in FIG. 1, the counter 112 counting the range of the site, the generator 110 addresses the memory 108 to provide the set of multiplying factors for a Fresnel pattern focussed at that site.

The sum produced by the summer 80 is multiplied in the mixer 84 by the cosinusoidal reference of the generator 58 on line 62, the mixer providing the difference between the reference frequency and the transmitted frequency in the output product. The mixer 85 operates in the same fashion as does the mixer 84 to provide the product of the sum of the summer 81 and the sinusoidal reference signal. As was mentioned earlier with reference to FIG. 6, the cosinusoidal reference on line 62 and the sinusoidal reference on line 64 are both at double the frequency of the carrier from the transmitted signal. The amplitudes of the products of the mixers 84 and 85 are equalized by the attenuators 88 and 89, the attenuators 88–89 being operated by the knob 94 for varying the attenuation of the product of the mixer 84 relative to that of the mixer 85 to produce the desired equalization. Thereupon, the attenuated signals as provided by the attenuators 88–89 are summed together by the summer 96 and coupled via the filter 98 to the display 56. The filter 98 has a pass band sufficiently wide to pass the sum signal of the summer 96 while attenuating harmonics thereof resulting from the action of the mixers 84–85. A graph within the block representing the filter 98 shows exemplary cut-off frequencies at $\frac{1}{2}$ and 3/2 of the transmitted frequency. The signal produced by the filter 98 represents the image of one of the sites in the subject 24 of FIG. 1 as is produced by the converging radiation pattern of FIG. 4, the diverging radiation pattern having been canceled out in the summer 96. The range counter 112 is coupled to the display 56 to provide a display of images of the sites by the filter 98 as a function of range provided by the summer 112.

Referring now to FIG. 8, the controller 100 is seen to comprise the memory 108, the address generator 110 and the range counter 112 which was previously seen in FIG, 7. In addition, the controller 100 comprises a switching matrix 114, a counter 116, buffer storage registers 118–119, a switch 122 and a digital inverter 124. The switching matrix 114 comprises a set of switches 126 and a set of switches 128. As noted hereinabove with reference to FIG. 7, the memory 108 stores sets of factors, these factors being presented graphically in FIG. 8 in a diagrammatic representation of the storage wherein individual rows correspond to depth of site as measured in the Y direction of the coordinate system 36 in FIG. 1. Thus, by way of example, a row corresponds to Y=20 mm, Y=40 mm with further rows corresponding to increments of 20 mm until the last row shown as Y=160 mm. Each row stores the factors for both the cosinusoidal Fresnel pattern and the sinusoidal Fresnel pattern, this corresponding to the odd numbered multipliers 76 and the even numbered multipliers 77 of FIG. 7. An address for addressing individual cells of the memory 108 is provided on line 130 from the generator 110. The stored data of the memory 108 is read-out on line 132 in response to the address on line 130, the stored data on line 132 being coupled by the switch 122 alternately to the register 118 and the register 119. As seen in FIG. 2, the number of active elements in the region of the array 22 used for forming the Fresnel focussing is represented by the letter K. In the example described with reference to the FIGS. 2 and 4, K is assumed equal to 60. Accordingly, instead of storing pairs of factors for all 260 elements of the array 22 of FIG. 2, the memory 108 stores pairs of factors for each of the 60 elements of the active region, this totaling 120 factors for each value of Y. Accordingly, each row of the memory 108 of FIG. 8 has 120 cells for storing the sixty factors of the cosinusoidal Fresnel pattern and the sixth factors of the sinusoidal Fresnel pattern. The desired factors are read out serially on line 132 but utilized simultaneously by the multipliers 76-77 of FIG. 7. The registers 118-119 provide buffer storage of these factors to permit both the serial read-out on line 132 and the simultaneous control of multiplication by signals at the terminals A1-AM.

The coupling of the factors from the line 132 to the terminals A of the controller 100 is accomplished as follows. The switches 128 select alternately data stored in the registers 118-119. The switches 128 are coupled to the same one of the registers 118-119. Thus, as seen in FIG. 8, a switch 128 is seen coupling signals from the register 118 and, accordingly, the switch 122 is seen coupling signals into the register 119. In this way, signals are read-out from the register 118 in parallel via the K output lines to respective ones of the switches 128 while the register 119 is being filled with new values of data stored in the memory 108. The output signals of the switches 128, shown on lines #1, #2 and #K are applied to respective ones of the switches 126. Each switch 126 is in the form of a multiple selector switch or multiplier and has a set of output terminals equal in number to the number of terminals A. Thereby, in response to a digital signal from the counter 116, each switch 126 couples the signal from its input terminal to one of the terminals A1-AM.

The operation of the switches 126 may be further explained by way of example. In response to clock pulses provided by the timer 50 at terminal C, the counter 116 counts successive range scans of a set of sites within the subject 24 such as the three sites shown in FIG. 1. Upon completion of each range scan, a clock pulse is applied to the input terminal of the counter 116, whereupon the counter advances its count to indicate the next position along the X axis of FIG. 1 for the next range scan along the Y axis of FIG. 1. The coupling of the switches 126 to the terminals A1-AM is accomplished in a manner whereby, in response to a digital signal representing a count of one from the counter 116, the first of the switches 126 couples the signal from line #1 to terminal A1, the second of the switches 126 couples the signal from line #2 to terminal A2, and similarly with the remaining ones of the K switches 126. In this way, the counter 116 in conjunction with the switches 126 accomplishes the side-stepping of the range scans along the X axis of FIG. 1 to produce the image in the form of a swath along the X axis of the subject 24.

The range counter 112, in response to clock pulses provided by the timer 50 by the terminal C, counts individual increments of range or depth along the Y axis of FIG. 1. The least significant bit drives the switches 128 and the switch 122 to accomplish the aforementioned alternation in the use of the registers 118 and 119. The logic state of the least significant bit changes state with each increment in range, these changes in state operating the switches 128 to accomplish the aforementioned switching between the registers 118-119. The least significant bit from the range counter 112 is coupled via the inverter 124 to the switch 122, the inverter 124 complementing the logic state so that the switch 122 is directed toward the register 119 while the switches 128 are directed to the register 118. Clocking of data through the registers 118-119 is accomplished by clock pulse signals from the timer 50 which are coupled via terminal C.

Figure 9:
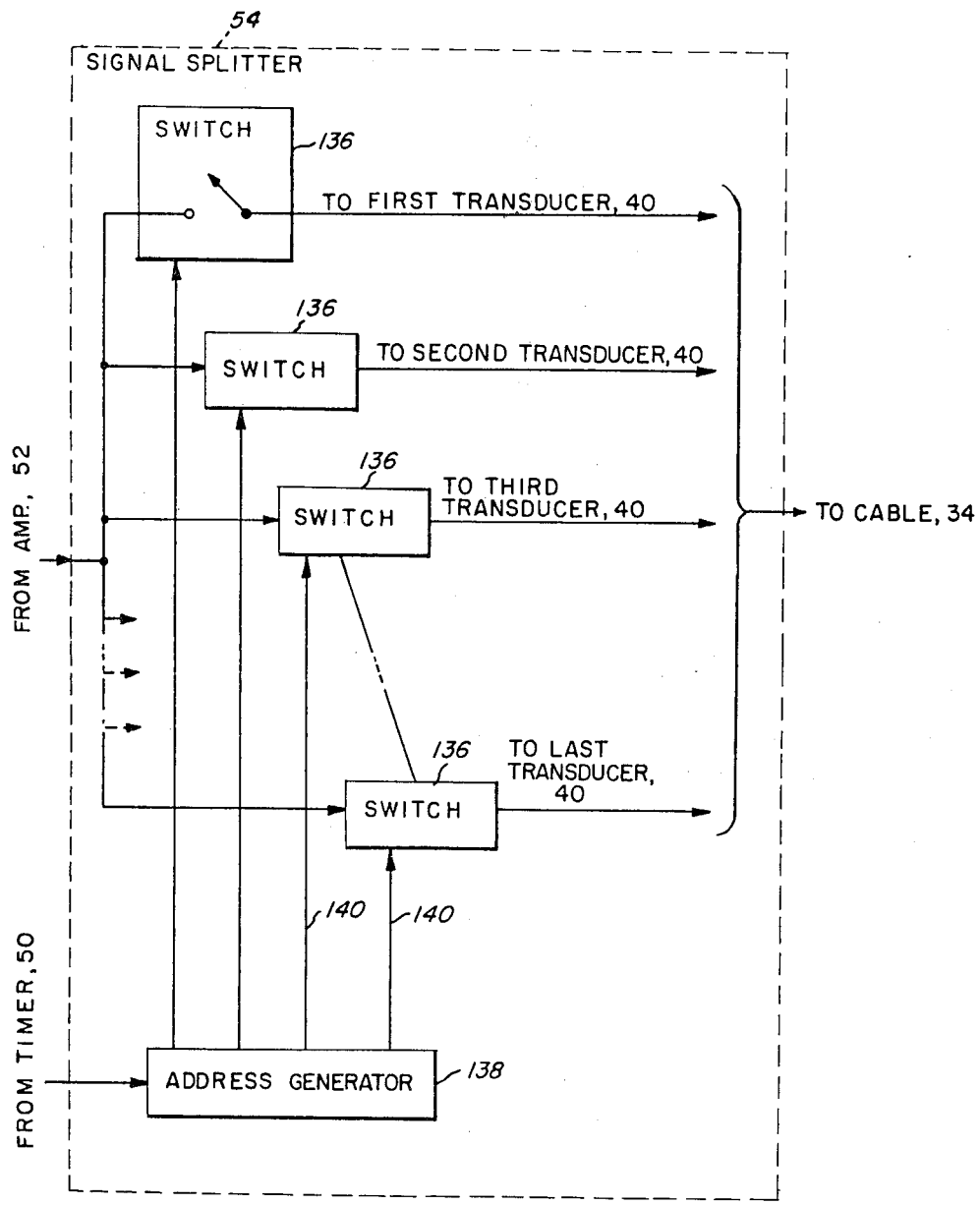
FIG. 9 is a block diagram of a signal splitter in the transmitter of FIG. 6 for transmitting a beam focussed at infinity.

Referring now to FIG. 9, the signal splitter 54 of FIG. 6 is seen to comprise a set of switches 136 coupled to respective ones of the transducers 40, and an address generator 138 coupled via lines 140 to individual ones of the switches 136. The generator 138, in response to the clock pulse signals from the timer 50, addresses individual ones of the switches, via the lines 140, to couple the signal from the amplifier 52 to the respective ones of the transducers 40. A group of four switches is addressed to energize the exemplary group of four transducers 40, shown in FIG. 3, for transmitting a beam of sonic energy. Groups of the switches 136 are addressed sequentially corresponding to the side-stepping of the group of transducers 40 of FIG. 3 for scanning the beam along the X coordinate system 36 of FIG. 1.

MATHEMATICAL DESCRIPTION

The foregoing system can be further described mathematically as follows. The signal received by one of the transducers, s(t,x), is given by $$s(t,x) = A(x) \cos(\omega t + \beta \phi_x) \tag{1}$$

where
 x is distance along the array,
 t is time,
 $\phi_x$ is a phase angle dependent on the x coordinate,
 $\omega$ is radian frequency and
 A(x) is amplitude dependent on the x coordinate.

The expression for the signal $s_c(t,x)$, passing through the cosine branch of FIG. 7 and appearing at the output of the mixer 84, assuming the true Fresnel pattern shown in the first graph of FIG. 4 rather than the square wave approximation shown in the second graph of FIG. 4, is given by $$s_c(t,x) = K_c A(x) \cos(\omega t + \phi_x) \cos(\beta x^2) \cos(2\omega t) \tag{2}$$

After dropping the high frequency term (3ω) which would be filtered out by the electrical circuitry, the baseband component $s_{cb}(t,x)$, is given by $$s_{cb}(t,x) = (K_c/2)A(x) \cos(\Omega t - \phi_x) \cos(\beta x^2) = (K_c/4)A(x) \cos(\omega t - \phi_x + \beta x^2) + (K_c/4)a(x) \cos(\omega t - \phi_x - \beta x^2) \tag{3}$$

where $K_c$ is an amplitude scale factor and β is a constant in the Fresnel term. The corresponding signals of the sine branch $s_s(t,x)$ and $s_{sb}(t,x)$, appearing at the output of the mixer 85 are given by $$s_s(t,x) = K_s A(x) \cos(\omega t + \phi_x) \sin(\beta x^2) \sin(2\omega t) \tag{4}$$

$$s_{sb}(t,x) = (K_s/2)A(x) \sin(\omega t - \phi_x) \sin(\beta x^2) = (K_s/4)A(x) \cos(\omega t - \phi_x - \beta x^2) - (K_s/4)A(x) \cos(\omega t - \phi_x + \beta x^2) \tag{5}$$

where $K_s$ is an amplitude scale factor.

Upon adjusting the attenuators 88 and 89 to equalize the amplitudes $K_cA(x)$ and $K_sA(x)$ of the signals of the cosine and sine branches, the sum of the signals of the cosine and sine branches, $v_{out}(t,x)$, appearing at the output of the summer 96 is given by the sum of Equations (3) and (5), namely, $$v_{out}(t,x) = KA(x)\cos(\omega t - \phi_x - \beta x^2) \qquad (6)$$

The expression of Equation (6) contains only one term with $\beta x^2$ while an extra term in $\beta x^2$ appears in both Equations (3) and (5). It is these extra terms which produce the undesired diverging beam of the prior art. When $\beta$ is adjusted so that $\phi_x = \beta x^2$, the transducers are focussed on a wave with curvature about the desired focal point. The above analysis describes receiver operation; for a transmitter, such as that to be described in FIG. 11, the mathematical analysis is similar.

This system can be made to dynamically focus, that is, the focal length of the transducer array can be changed, as noted hereinabove, as a function of time to track the return echoes. This is accomplished by changing the switches 106 of FIG. 6 in time so the quadratic term $\beta x^2$ matches the curvature of the returning echoes.

FOCUSSED TRANSMISSION

Figure 10:
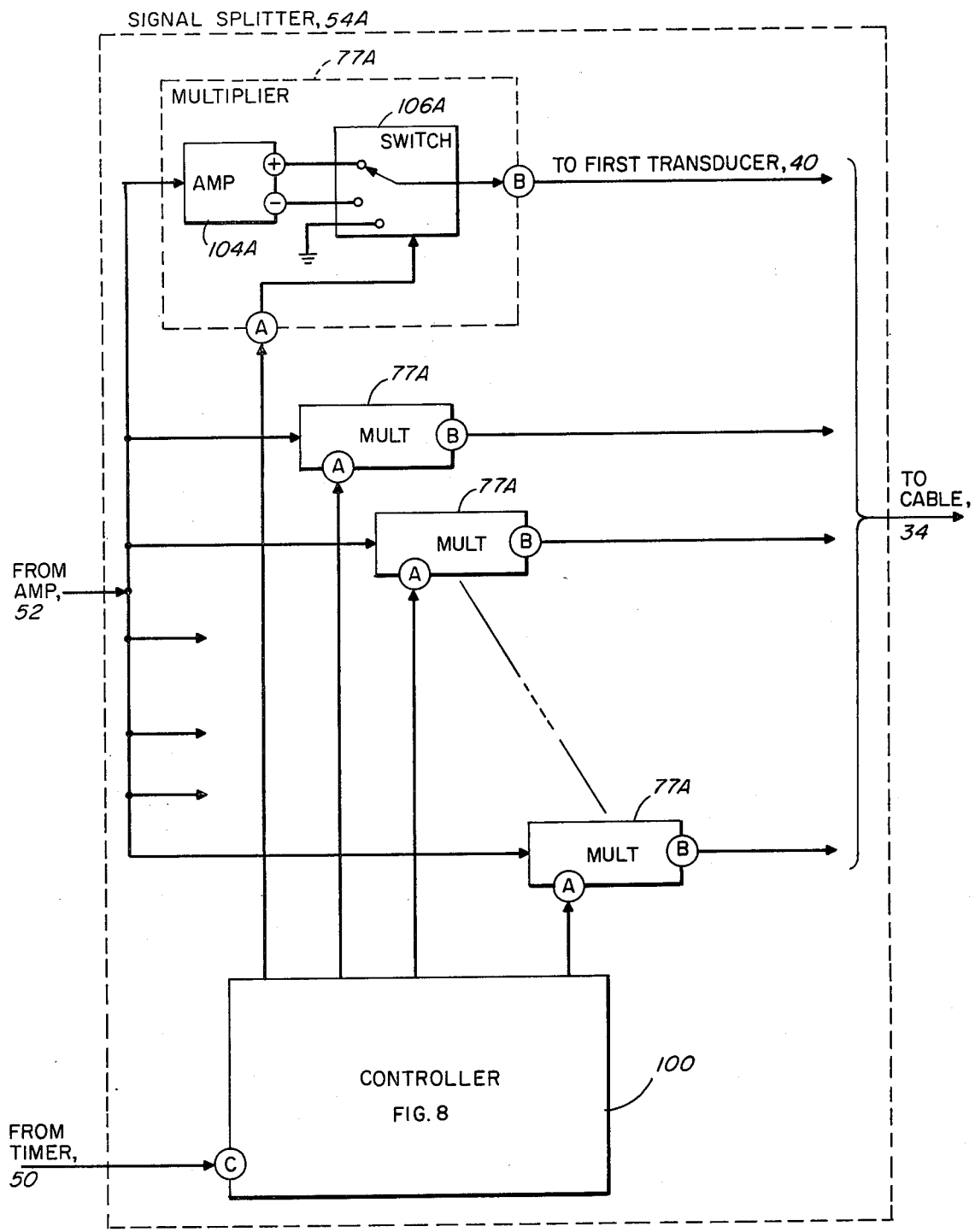
FIG. 10 is a block diagram of an alternative embodiment of the signal splitter of FIG. 9 providing a Fresnel weighting for focussing the signal within the subject.

Referring now to FIG. 10, there is seen an alternative embodiment of the signal splitter 54 of FIG. 9, this alternative embodiment being identified by the legend 54A in FIG. 10. The signal splitter 54A provides for improved transmission of sonic energy as compared to the operation of the signal splitter 54, the signal splitter 54A providing for the focussing of the sonic energy at the sites in the subject 24 of FIG. 1 while, with the foregoing use of the signal splitter 54 in FIG. 6, the sonic energy is focussed at infinity. The signal splitter 54A comprises multipliers 77A and the controller 100 of FIGS. 7 and 8. The multipliers 77A differ from the multiplier 77 of FIG. 7, the multiplier 77A comprising an amplifier 104A and a switch 106A which are adapted for handling relatively high signal power for the transmission of sonic energy while the amplifier 104 and the switch 106 of the multiplier 77 of FIG. 7 are adapted for use with the relatively low signal power of signals received by the transducers 40. The multipliers 77A of FIG. 10 are controlled by the controller 100 in response to clock signals by the timer 50 in a manner analogous to the controlling of the multipliers 77 of FIG. 7 by the controller 100 as is explained hereinabove.

Figure 12:
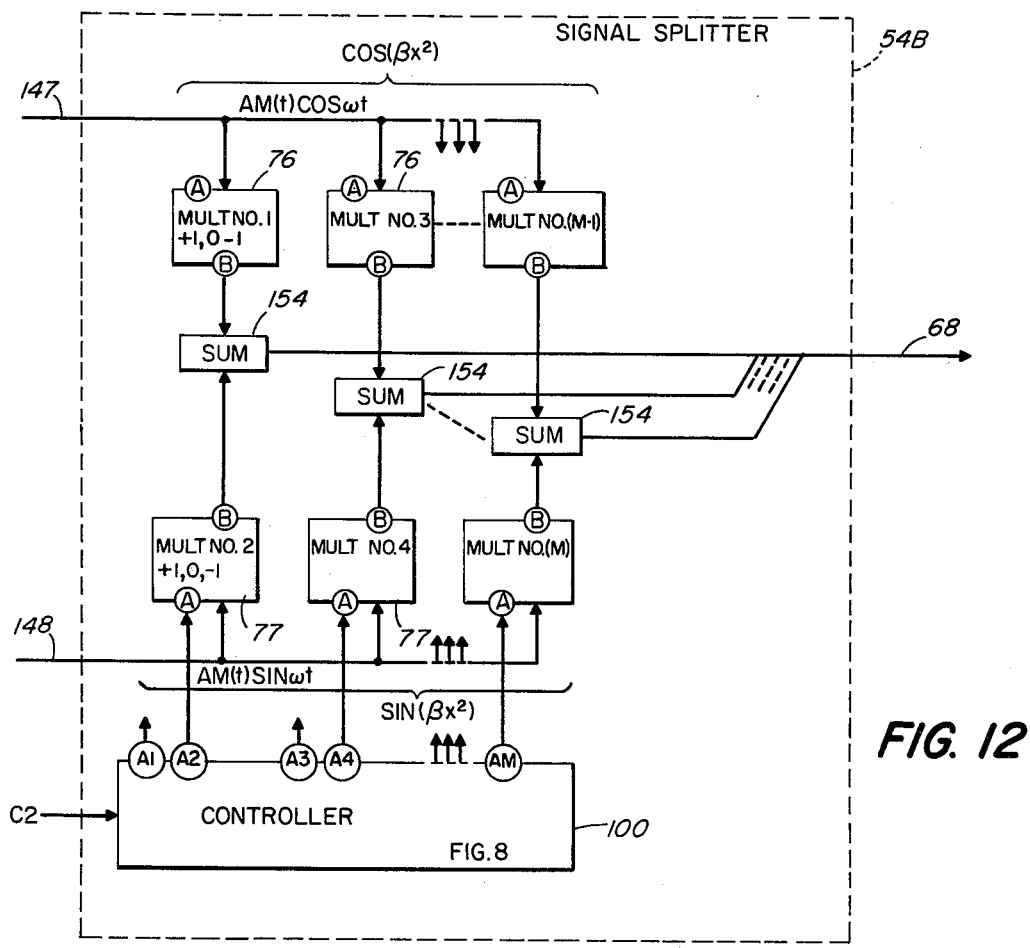
FIG. 12 is an alternative embodiment of a signal splitter for weighting the sinusoidal and cosinusoidal signal components for the transmitter of FIG. 11.

Since the signal splitter 54A comprises only one set of multipliers 77A, this corresponding to the sine branch of FIG. 7, the phasing of the transducer signals follows that portrayed in the third graph of FIG. 4. Thus, the signal splitter 54A when utilized in the transmitter 30 of FIG. 6, in lieu of the signal splitter 54, produces the square wave approximation to the Fresnel function as described in FIG. 4. As a result, a portion of the sonic radiation converges on the real focal point at one of the sites in the subject 24 of FIG. 1 while the remaining portion diverges from a virtual focus behind the array 22 of FIGS. 1 and 4. The number of transducer elements 40 of FIG. 3 utilized for transmission with the signal splitter 54A, as well as that to be described hereinafter with reference to the signal splitter 54B of FIGS. 11 and 12, is advantageously made the same as that utilized in the group of receiving elements designated by the letter R in FIG. 3. Thereby, the aperture size of the active elements of the array 22 is the same on both receiving and transmitting for an equal focussing capability.

Referring now to FIG. 11, there is seen the transducer array 22, the amplifier system 26 and the receiver 32 as disclosed previously with reference FIG. 6. In addition, a transmitter 30A, in lieu of the transmitter 30 of FIG. 6, is shown coupled between the receiver 32 and the amplifier system 26. The transmitter 30A differs from the transmitter 30 in that a pair of modulators 48 and a pair of amplifiers 52A are utilized in lieu of the single modulator 48 and the single amplifier 52 of FIG. 6. In addition, a signal splitter 54B, to be further described with reference to FIG. 12, is shown receiving signals from the amplifiers 52A, the signal on line 147 corresponding to the cosine branch, and the signal on line 148 corresponding to the sine branch as disclosed previously with reference to FIG. 7. The amplifier 52A functions in the manner of the amplifier 52 of FIG. 6, but further includes a gain control terminal whereby the gain of the amplifier 52A may be varied. A knob 150 coupled to the gain control terminals of each of the amplifiers 52A via a mechanical connection represented by line 152 decreases the gain of one of the amplifiers 52A while increasing the gain of the other of the amplifiers 52A. Thereby, rotation of the knob 150 permits equalization of the amplitudes of the signals provided at the output terminals of the two amplifiers 52A. Mathematical expressions for the signals of the cosine and sine branches are shown in FIG. 11 adjacent the lines coupling the signals from the amplifiers 52A to the signal splitter 54B. In the mathematical expressions, the term A represents the amplitude of the signal while the term M(t) represents the modulation applied by a modulator 48. In the cosine channel, the modulation is applied to the cosinusoidal carrier signal on line 60 while the modulation for the sine channel is applied to the sinusoidal carrier signal on line 61.

Referring to both FIGS. 11 and 12, the output signal of the signal splitter 54B on line 68 is a composite of the signals of the cosine branch and sine branch which is produced in a manner analogous to the previously described operation of FIG. 7. Since the signal on line 68 now contains components of both the cosinusoidal and sinusoidal Fresnel patterns, the resultant distribution of signals across the radiating aperture of the array 22 provides for a focussing of the transmitted sonic energy toward a real focal point in the subject 24 of FIG. 1 without the production of the undesired diverging beam of sonic energy from the virtual focus behind the array 22 as resulted from the use of the signal splitter 54A of FIG. 10. The undesired diverging beam of sonic energy is removed by the cancellation of the extra term in $\beta x^2$ as has been explained with reference to Equation 6 hereinabove.

In FIG. 12 the signal splitter 54B is seen to comprise multipliers 76 and 77 and the controller 100 which were previously described with reference to FIG. 7. In addition, the signal splitter 54B comprises a set of summers 154 which are coupled to the output terminals of the multipliers 76 and 77 for combining the respective signals, the lines from the output terminals of the summers 154 being shown fanning into the line 68 for coupling to respective ones of the transducers 40 of the array 22 of FIG. 11. Signals of the cosine branch are multiplied by factors in accordance with the cosinusoidal Fresnel pattern, these factors being applied by the multipliers 76. Similarly, the multipliers 77 provide the sinusoidal Fresnel weighting factors to the signal of the sine branch. The multipliers 76–77 are activated by the controller 100 as was previously disclosed with reference to the FIGS. 7 and 8.

Figure 13:
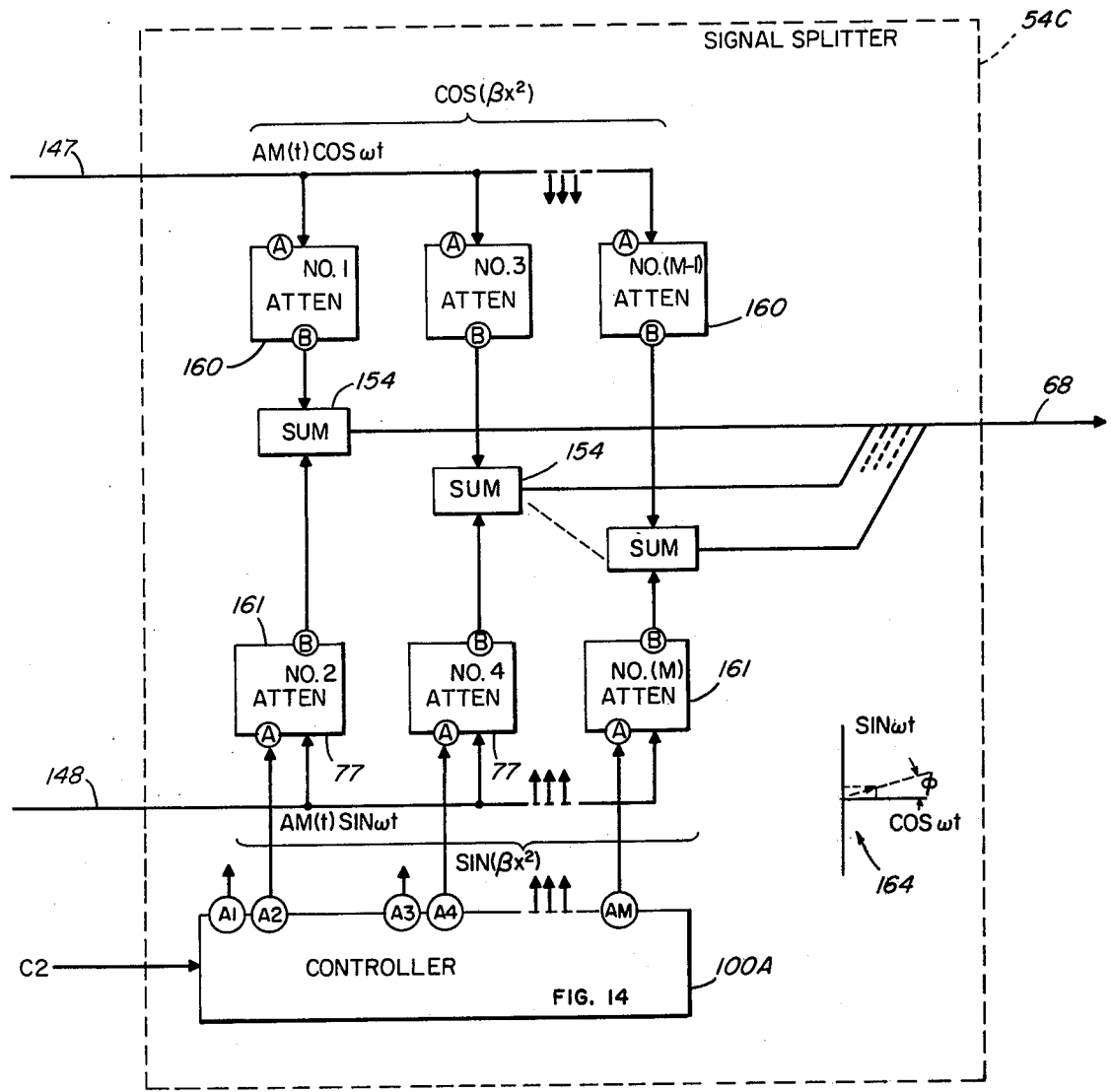
FIG. 13 is yet another embodiment of the signal splitter for the transmitter of FIG. 11 showing weighting by attenuators.

Referring now to FIG. 13, there is shown yet a further embodiment of the signal splitter of FIG. 6 for providing further accuracy to the aforementioned approximation, this further embodiment being identified by the legend 54C. The signal splitter 54C of FIG. 13 functions in a manner analogous to that of the signal splitter 54B of FIG. 12 and differs therefrom by the introduction of attenuators 160-161 in lieu of the multipliers 76–77 of FIG. 12. While the multipliers 76–77 are restricted to amplitudes of ±1, the attenuators 160–161 may provide any one of a large number of amplitudes. For example, in the event that the digital implementation of the attentuators 160 and 161 is utilized, amplitudes in increments of a quarter of the full amplitude, or even finer increments may be employed. Thus, with reference to the graph 164 located adjacent an attenuator 161 in FIG. 13, the vectors representing the signals of the cosine branch and the sine branch may be varied in amplitude by a small increment or a large increment to provide a resultant vector which may vary over a multiplicity of values from a value of unity to a value of zero with phase angles $\psi$ ranging from 0° to 360°. The resulting approximation is partially sketched in the second graph of FIG. 4 by the dashed line 166. The attenuated components are applied by the respective attenuators 160–161 to a summer 154 to produce the desired signal amplitude and phase for each one of the transducers 40 of the array 22. Thus, each transducer 40 of the radiating aperture of the array 22 receives a specific value of signal amplitude and signal phase for an accurate reproduction of the Fresnel pattern of the first graph of FIG. 4. In this way, a precisely focussed beam of sonic energy is produced by the system of FIG. 11 employing the signal splitter 54C of FIG. 13 in lieu of the signal splitter 54B shown in FIG. 11. The precisely focussed beam of sonic energy is directed to a site within the subject 24.

Figure 14:
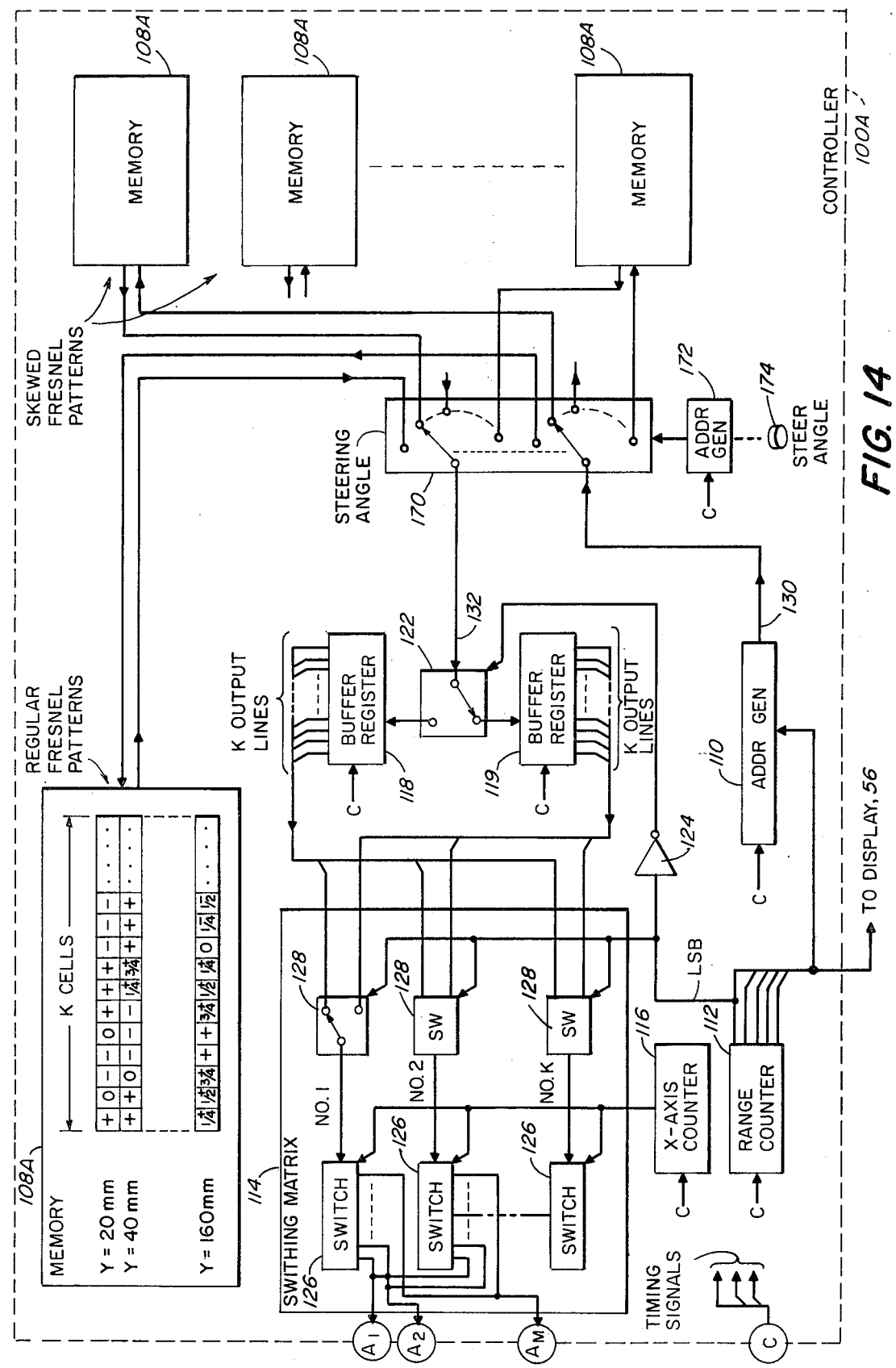
FIG. 14 is an alternative embodiment of the controller of FIG. 8 for steering a radiation pattern of the array of FIG. 1, the controller of FIG. 14 being used in the signal splitter of FIG. 13.
Figure 15:
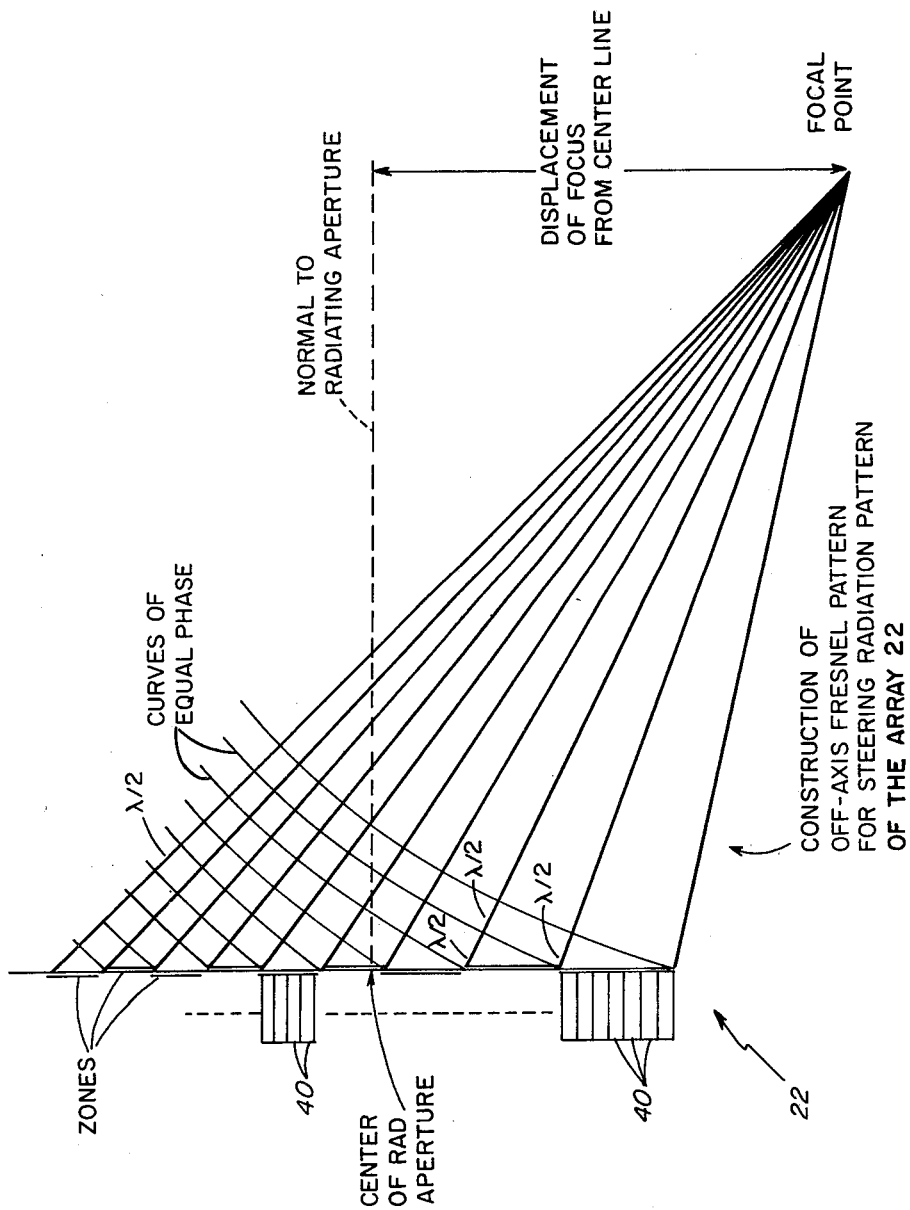
FIG. 15 is a diagram of a Fresnel construction for a focal point situated away from a normal to the radiating aperture of the array.

Referring also to FIGS. 14 and 15, a controller 100A of FIG. 13 is described. The controller 100A provides the functions previously described with reference to the controller 100 of FIG. 8 but, in addition, incorporates further memories 108A for steering the radiation pattern of the array 22 to provide focal points of radiant energy of the array 22 which are situated away from a normal to the center of the radiating aperture. Each of the memories 108A provides storage functions analogous to that previously described with reference to the memories 108 of FIG. 8 but, in addition, includes further storage space for storing the additional amplitude values as are produced by the attenuators 160–161 of FIG. 13. As shown in FIG. 14, one of the memories 108A produces a regular, or on-axis, Fresnel pattern for a focal point located on the normal to the radiating aperture while a set of other memories 108A are utilized for storing the attenuation factors for the signals of the transducers 40 for focal points which are situated off the normal to the radiating aperture. As seen in FIG. 15, such a focal point produces a skewed pattern which has the form of an off-axis Fresnel pattern. With respect to the set of memories 108A producing the skewed Fresnel patterns, a separate memory is utilized for each displacement of the focal point from the normal to the radiating aperture.

In addition, to the compounds previously described with reference to FIG. 8, the controller 100A of FIG. 14 further comprises a switch 170 coupled to each of the aforementioned memories 108A, an address generator 172 for directing the switch 170 to the desired one of the memories 108A, and a knob 174 coupled to the generator 172 for either manually selecting a specific steering angle of the radiation pattern, or for permitting the generator 172 to automatically scan the steering angle. The switch 170 couples the lines 130 and the lines 132, previously described in FIG. 8, to the selected one of the memories 108A for producing a focus situated on the aforementioned normal or at a predetermined distance from the normal. In response to signals from the address generator 110, the selected memory 108A provides the desired attenuation factors to the registers 118-119 via switch 122 for storing the attenuation values in the manner previously described for the multiplying factors in FIG. 8. The generator 172 is responsive to clock pulses at terminal C for sequentially positioning the arms of the switch 172 to scan the radiation pattern in angle or, altenatively as noted above, the generator 172 addresses the switch 170 to a specific steering angle as designated by the knob 174.

It is understood that the above-described embodiments of the invention are illustrative only and that modifications thereof may occur to those skilled in the art. Accordingly, it is desired that this invention is not to be limited to the embodiments disclosed herein but is to be limited only as defined by the appended claims.

What is claimed is:

1. An imaging system comprising:
   an array of radiating elements oriented toward a subject for communicating radiant energy between said array and a site within said subject;
   first means for generating a first group of signals modulated in the format of a cosinusoidal Fresnel pattern;
   second means for generating a second group of signals modulated in the format of a sinusoidal Fresnel pattern;
   corresponding signals of each of said groups being coupled to respective ones of said radiating elements; and
   means for combining said corresponding signals to form a Fresnel signal pattern for said array to provide a focal point for said radiant energy adjacent said array.

2. A system according to claim 1 further comprising means for selecting a portion of said array to which said corresponding signals are coupled and means for coupling said corresponding signals to said selected portion, said selecting means including means for successively altering selected portions of said array for scanning said subject.

3. A system according to claim 1 wherein said first and said second generating means includes means for altering said cosinusoidal and said sinusoidal Fresnel patterns to vary the distance of said focal point from said array.

4. A signal processor for coupling signals to an array of radiating elements for focussing radiant energy of said array at a point adjacent said array, said processor comprising:
   means for modulating signals of respective ones of said elements in accordance with formats approximating sinusoidal and cosinusoidal Fresnel patterns; and means coupled to said modulating means for combining the modulated signals for each of said elements to provide a focal point of said radiant energy.

5. A processor accordig to claim 4 further comprising means coupled to said modulating means for selecting the signals of specific ones of said radiating elements to scan said focal point through a subject faced by said array.

6. A processor according to claim 5 further comprising means coupled to said modulating means for displaying an image of said subject, and a transmitter including second modulating means for modulating signals for said radiating elements in the format of sinusoidal and cosinusoidal Fresnel patterns for focussing transmitted radiant energy at a predetermined focal point in said subject.

7. A processor according to claim 4 further comprising means for displacing said focal point from a normal to the center of the radiating aperture of said array.

* * * * *

UNITED STATES PATENT OFFICE
CERTIFICATE OF CORRECTION

Patent No. 4,320,660    Dated March 23, 1982

Inventor(s) Roger H. Tancrell

It is certified that error appears in the above-identified patent and that said Letters Patent are hereby corrected as shown below:

Column 1, line 65, delete --the-- and insert --for--;

Column 8, line 10, delete --range of depth-- and insert --range or depth--;

Column 8, line 11, delete --in FIG. 1-- and insert --of FIG. 1--

Column 9, line 16, delete --sixth-- and insert --sixty--;

Column 10, line 57, delete --($\Omega$t)-- and insert --(wt)--;

Column 10, line 58, delete --a-- (second occurrence) and insert --A--;

Column 10, line 62, delete --ss-- and insert --$s_s$--;

UNITED STATES PATENT OFFICE
CERTIFICATE OF CORRECTION

Patent No. 4,320,660      Dated March 23, 1982

Inventor(s) Roger H. Tancrell

It is certified that error appears in the above-identified patent and that said Letters Patent are hereby corrected as shown below:

Column 11, line 16, delete -- $-Bx^2$ -- and insert -- $= -Bx^2$ --;

Column 11, line 24, delete --FIG. 6-- and insert --FIG. 7--;

Column 12, line 5, after --reference-- insert --to--;

Column 14, line 1, delete --compounds-- and insert --components--;

Column 14, line 17, after --via-- insert --the--;

Column 15, line 2, delete --for-- and insert --of--;

Column 15, line 4, delete --accordig-- and insert --according--

Signed and Sealed this

Twentieth Day of July 1982

[SEAL]

Attest:

GERALD J. MOSSINGHOFF

Attesting Officer     Commissioner of Patents and Trademarks